US00PP13867P39

(12) United States Plant Patent
Miyazaki

(10) Patent No.: US PP13,867 P3
(45) Date of Patent: Jun. 10, 2003

(54) PETUNIA PLANT NAMED 'SUNLAPUR'

(75) Inventor: Kiyoshi Miyazaki, Hikone (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/878,237

(22) Filed: Jun. 12, 2001

(65) Prior Publication Data

US 2002/0188995 P1 Dec. 12, 2002

(51) Int. Cl.[7] ..... A01H 5/00
(52) U.S. Cl. ..... Plt./356
(58) Field of Search ..... Plt./356

(56) References Cited

U.S. PATENT DOCUMENTS

| | | | |
|---|---|---|---|
| PP6,899 | P | 7/1989 | Tsuda et al. |
| PP6,914 | P | 7/1989 | Tsuda et al. |
| PP6,915 | P | 7/1989 | Tsuda et al. |
| PP8,489 | P | 12/1993 | Hirabayashi et al. |
| PP8,768 | P | 6/1994 | Hirabayashi et al. |
| PP9,322 | P | 10/1995 | Tachibana et al. |
| PP9,341 | P | 10/1995 | Tachibana et al. |
| PP9,342 | P | 10/1995 | Sakazaki et al. |
| PP9,556 | P | 5/1996 | Tachibana et al. |
| PP9,557 | P | 5/1996 | Suzuki et al. |
| PP9,754 | P | 12/1996 | Suzuki et al. |
| PP10,278 | P | 3/1998 | Murakami |
| PP10,279 | P | 3/1998 | Murakami |
| PP10,287 | P | 3/1998 | Murakami |
| PP10,310 | P | 3/1998 | Sakazaki |
| PP10,330 | P | 4/1998 | Sakazaki |
| PP10,355 | P | 4/1998 | Murakami |
| PP10,904 | P | 5/1999 | Hansson |
| PP11,352 | P | 4/2000 | Murakami |
| PP11,558 | P | 10/2000 | Murakami |

OTHER PUBLICATIONS

UPOV–ROM GTITM Computer Database, 2001/06, GTI Jouve Retrieval Software, citation for 'Sunlapur'.*

* cited by examiner

*Primary Examiner*—Bruce R. Campell
*Assistant Examiner*—Susan B. McCormick
(74) *Attorney, Agent, or Firm*—Burns, Doane, Swecker & Mathis, L.L.P.

(57) ABSTRACT

'SUNLAPUR' is a decumbent plant, with very large and vivid purplish red flowers, which is suitable for potting and flower bedding. The spreading area of the plant is very large. This plant has abundant branching. The length of internodes is 2.8 cm.

The leaf shape is lanceolate with some pubescence on the surface, having small petiole. Leaf color is dark green.

The flowers are single and very large. Facing direction of flowers is slightly upward to horizontal. Ground color of flower is vivid reddish purple with dark purple vein. The bottom color of inside of throat is strong purple and the outside color of corolla tube is reddish purple. Shape of petal tip is acute, lobation is deep, and waving is medium.

The plant exhibits early flowering. It has a high resistance to rain, heat, disease and moderate resistance to pests.

2 Drawing Sheets

BOTANICAL/COMMERCIAL CLASSIFICATION

*Petunia hybrida*/Petunia Plant

VARIETAL DENOMINATION cv. 'Sunlapur'.

BACKGROUND OF THE VARIETY

The Petunia is a very popular plant that is used for flower bedding and potting in the summer season. There are only a few Petunia varieties which do not have an upright growth habit and which have a high resistance to rain, heat, cold, and diseases. The Petunias of the Revolution series include 'Revolution Purplepink' (U.S. Plant Pat. No. 6,915), 'Revolution Brilliantpink' (U.S. Plant Pat. No. 6,914), 'Revolution Brilliantpink-mini' (U.S. Plant Pat. No. 6,899), and 'Revolution Bluevein' (U.S. Plant Pat. No. 9,322). These are decumbent type plants having long stems, a lower plant height, abundant branching, and a high resistance to heat, cold and rain. However, there are only a few Petunia varieties having a great profusion of flowers, large vivid reddish-purple colored flowers, and a high resistance to rain, heat, cold and diseases. Accordingly, this invention was aimed at obtaining a new Petunia variety having a vivid reddish-purple colored flowers, together with the above features.

The new variety of Petunia plant according to this invention originated in April 1995 from crossing as male parent a wild-type Petunia plant native to Brazil (non-patented in the United States) which had decumbent habit, and as a female parent the cultivar 'Titan Red' (non-patented in the United States). From that crossing, 384 seedlings were obtained and evaluated in July 1995. A trial involving potted plants was carried out and 15 seedlings were selected. These 15 seedlings were propagated by the use of cuttings and were grown in a trial in flower beds and in containers. The botanical characteristics of these plants were examined using the similar varieties 'Revolution Brilliantpink' and 'Revolution Brilliantpink-mini' for comparison. Finally, a single Petunia plant was selected in December 1996. It was concluded that this new variety is distinguishable from other varieties especially with respect to flower size, and this variety of Petunia plant was named 'Sunlapur'.

This new variety of Petunia plant named 'Sunlapur' was asexually reproduced by the use of cuttings at Oomori-cho, Yokaichi-shi, Shiga-ken, Japan, and the homogeneity and stability thereof were confirmed. It commonly takes approximately one week to initiate the rooting of cuttings of the new variety of the present invention.

In the following description, the color identification is in accordance with The R.H.S. Colour Chart of The Royal Horticultural Society, London, England.

SUMMARY OF THE NEW VARIETY

Described herein is a decumbent type Petunia plant named 'Sunlapur' having very large vivid reddish-purple flowers. The plant has abundant branching, a great profusion of blooms, and the entire plant remains in bloom for a considerable period of time. The plant is highly resistant to rain, heat, cold and disease. This new variety of Petunia plant is suitable for growing in pots, hanging baskets, and flower beds.

The plants described and depicted herein were propagated by the use of cuttings. Following rooting the plants were transplanted into small pots in a greenhouse, and were subsequently transplanted into larger pots and were grown outside. Such plants were approximately 12 weeks of age from the time of the rooting of cuttings.

DESCRIPTION OF THE NEW VARIETY

Figure 1:
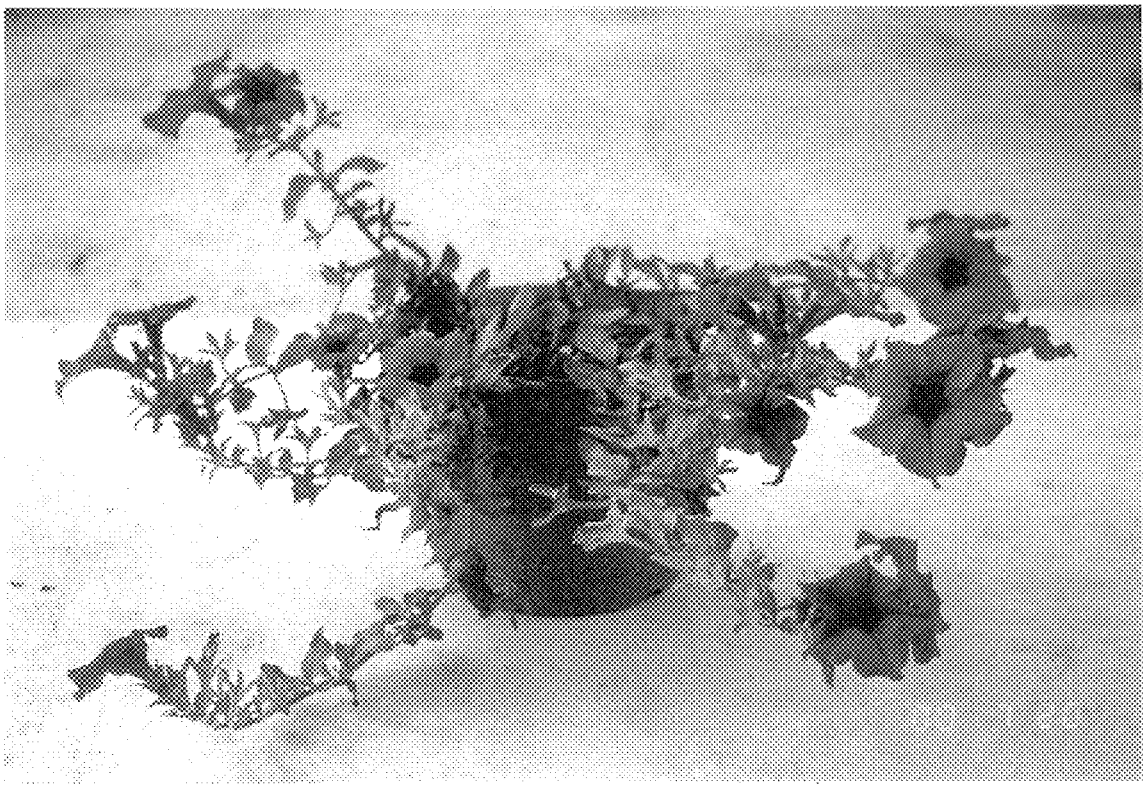
FIG. 1 is photograph giving a partial view of the new variety of Petunia plant named 'Sunlapur'.
Figure 2:
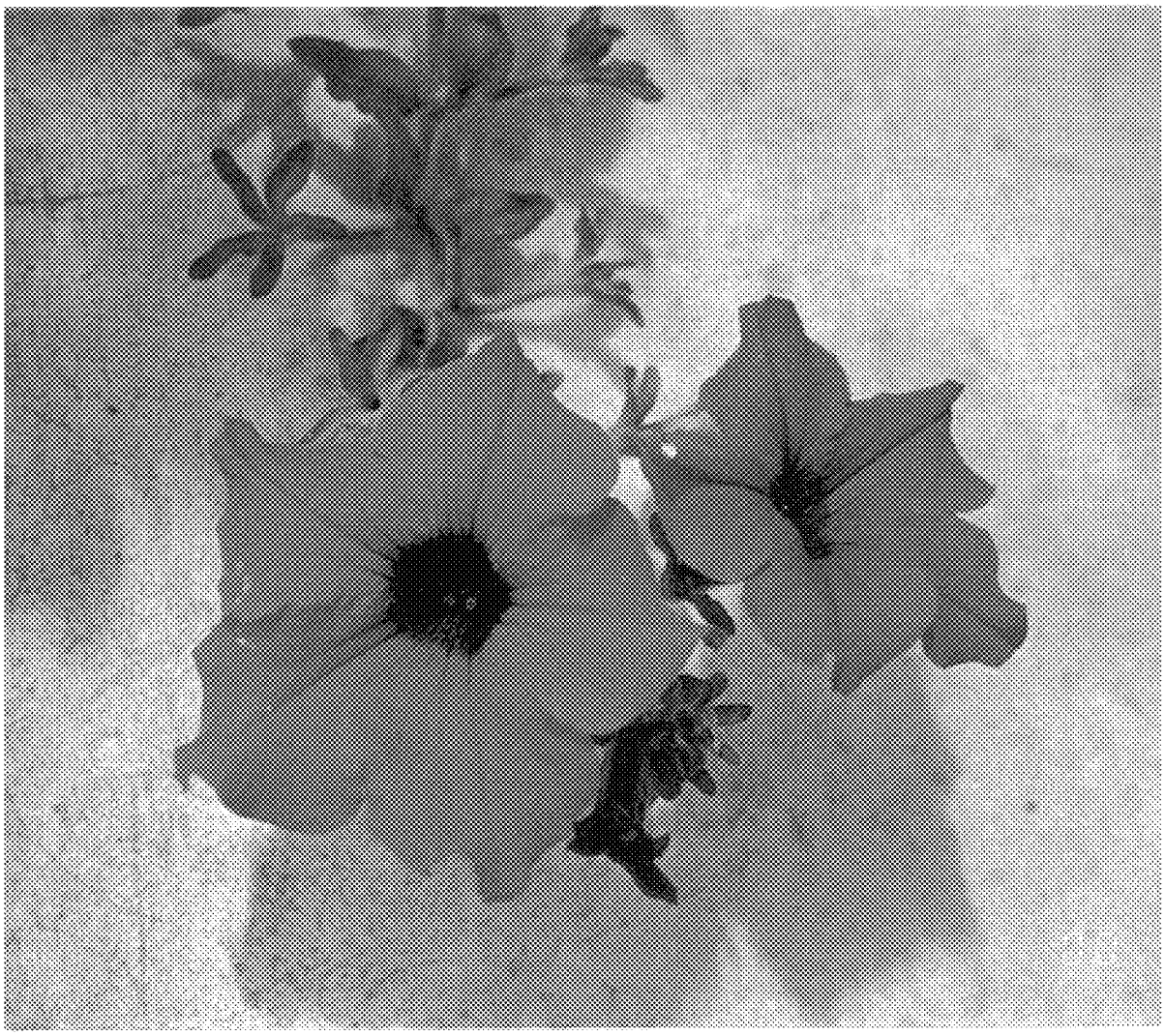
FIG. 2 is a photograph of flowers of the new variety of Petunia plant named 'Sunlapur'.

The new variety of Petunia plant 'Sunlapur' is different from the similar variety, 'Revolution Brilliantpink' in the following areas:

1. The length of main stem from the base to the first flowering node of 'Sunlapur' is approximately 14 cm and is shorter than the approximately 50 cm length of 'Revolution Brilliantpink'.
2. There is no anthocyanin coloration on the stem of 'Sunlapur' compared to the stem of 'Revolution Brilliantpink' that displays some anthocyanin coloration.
3. The shape of leaves of 'Sunlapur' is lanceolate compared to the leaves of 'Revolution Brilliantpink' that are elliptic.
4. The attaching angle of the upper leaf of the main stem of 'Sunlapur' is horizontal to droopy compared to that of 'Revolution Brilliantpink' that is attached slightly upward to the horizontal.
5. The surface color of leaves of 'Sunlapur' is dark green (R.H.S. No. 137A) compared to the color of 'Revolution Brilliantpink' which is dark yellowish-green (R.H.S. No.146A).
6. The flower size of 'Sunlapur' is larger than that of 'Revolution Brilliantpink'.
7. The flower color of 'Sunlapur' is vivid reddish-purple (R.H.S. No. 74A) with a dark purple vein (R.H.S. No.79B) compared to the flower color of 'Revolution Brilliantpink' that is vivid reddish-purple (R.H.S. No. 74A) without a pattern.
8. The base color of the inside of the throat of 'Sunlapur' is strong purple (R.H.S. No. 83D) compared to 'Revolution Brilliantpink' that is dark grayish-purple (R.H.S. No. 79A).
9. The outside color of the corolla tube of 'Sunlapur' is reddish-purple (R.H.S. No. 77A) compared to 'Revolution Brilliantpink' that displays deep purplish-pink (R.H.S. No. 70C).
10. The lobation of the petals of 'Sunlapur' is deeper than that of 'Revolution Brilliantpink'.

The new variety of Petunia plant 'Sunlapur' is different from a similar variety, 'Revolution Brilliantpink-mini' in following areas:

1. The pubescence of the leaf of 'Sunlapur' is thicker than that of 'Revolution Brilliantpink-mini'.
2. The flower size of 'Sunlapur' is larger than that of 'Revolution Brilliantpink-mini'.
3. The flower color of 'Sunlapur' is vivid reddish-purple (R.H.S. No. 74A) with dark purple vein (R.H.S. No. 79B) compared to the flower of 'Revolution Brilliantpink-mini' that displays strong reddish-purple (R.H.S. No. 72A) with a dark grayish-purple vein (R.H.S. No. 79A).
4. The base color of the inside of the throat of 'Sunlapur' is strong purple (R.H.S. No. 83D) as compared to the throat of 'Revolution Brilliantpint-mini' that displays moderate purple (R.H.S. No. 83B).
5. The outside color of corolla tube of 'Sunlapur' is reddish-purple (R.H.S. No. 77A) compared to 'Revolution Brilliantpint-mini' that displays strong reddish-purple (R.H.S. No. 77B).
6. The shape of petal tip of 'Sunlapur' is acute compared to that of 'Revolution Brilliantpink mini' that is more obverse.
7. The lobation of the petals of 'Sunlapur' is deeper than that of 'Revolution Brilliantpink-mini'.
8. The pistils and stamens of 'Sunlapur' are thinner than those of 'Revolution Brilliantpink-mini'.

The vigor of the new plant of the present invention is good. In early summer a new plant commonly forms approximately 15 cm of new growth in a single week.

'Sunlapur' is a decumbent plant, with very large and vivid reddish-purple flowers, which is suitable for potting and growing in flower beds. The spreading area of the plant is very large with a mature plant commonly having a width of 50 cm, and the plant height is approximately 11.5 cm at the blooming time of the 5th to the 10th flower. The stem diameter is approximately 2.8 mm, and the coloration is green (R.H.S. 137C) with no anthocyanin coloration being present. The plant possesses abundant branching commonly with approximately 12 lateral branches per plant. The internode length commonly is approximately 2.8 cm.

The leaves are medium in size, approximately 66 mm in length, approximately 27 mm in width, and approximately 0.4 mm in thickness. Leaf shape is lanceolate, with some pubescence on the surface, and with a small petiole having a length of approximately 4 mm and a diameter of approximately 2.5 mm. The leaf color is dark green (R.H.S. No. 137A) on the upper surface yellow-green (R.H.S. 146B) on the under surface, the leaf apex is acute, and the leaf base acuminate. The leaves are pinnately veined.

The flower buds are tubular in configuration, and commonly measure approximately 45 mm in length and approximately 9 mm in diameter. The bud coloration is deep reddish-purple (R.H.S. 77A).

The calyx is tubular in configuration, approximately 24 mm in length, and divides into five sepals. The sepal coloration is yellow-green (R.H.S. 144A), and the sepal width commonly is approximately 11 mm at the broadest point.

The flowers are single, gamopetalous with five lobes, and very large with a diameter of approximately 10 cm. A typical corolla tube is approximately 35 mm in length. The facing direction of flowers is slightly upward to horizontal, and the flowers commonly display a diameter of approximately 10 cm. The ground color of flower is vivid reddish-purple (R.H.S. No. 74A) on the upper surface with a dark purple (R.H.S. No. 79B) vein. The base color of the inside of throat is strong purple (R.H.S. No. 83D) and the outside color of corolla tube is reddish-purple (R.H.S. No. 77A). The petal coloration on the under surface is strong reddish-purple (R.H.S. 78B). The shape of petal tip is acute, the lobation is deep, the margins are entire, and level of waviness is medium. The tubular shape of the calyx is typical for the species. The shape of the stamen is typical for the species, and 5 stamens are present. The filaments are light purple (R.H.S. 75A) in coloration, and commonly measure approximately 25 mm in length. The anthers are versatile and are brilliant violet (R.H.S. 94C) in coloration. The shape of the single pistil is typical for the species. The stigma and anthers tend to be curved in their disposition. The pistil commonly measures approximately 22 mm in length. The coloration of the stigma is yellow-green (R.H.S. 137C). The coloration of the style is light yellow-green (R.H.S. 150C). The position of the ovary is super-hypogynous and the ovary coloration is strong yellow-green (R.H.S. 144A). The length of the peduncle is approximately 21 mm, and the diameter is approximately 1.6 mm.

During observations to date fruits and seed are rarely formed. The fruit when formed is approximately 7 mm in length and approximately 5 mm in width. The immature fruit is strong yellow-green (R.H.S. 144A) in coloration. Mature seeds are reddish-brown (R.H.S. 165A) in coloration.

The plant exhibits early flowering. It also displays a high resistance to rain, heat, and disease, and a moderate resistance to pests. More specifically, during observations to date the plant has proven to be resistant to Powdery Mildew and Botrytis. Moderate resistance to Thrips and Mites has been observed.

What is claimed is:

1. The new and distinct variety of Petunia plant, substantially as herein illustrated and described, characterized particularly as to novelty by (A) a decumbent growth habit, (B) abundant branching with a great profusion of blooms and the entire plant remaining in bloom for considerable period of time, (c) very large single flowers having a vivid reddish-purple coloration with a dark purple vein, and (D) high resistance to rain, heat, Powdery Mildew, and Botrytis.

* * * * *

UNITED STATES PATENT AND TRADEMARK OFFICE

CERTIFICATE OF CORRECTION

PATENT NO. : PP 13,867 P3
DATED : June 10, 2003
INVENTOR(S) : Kiyoshi Miyazaki

It is certified that error appears in the above-identified patent and that said Letters Patent is hereby corrected as shown below:

Column 1,
Item [73], delete "[73] Assignee: Suntory Limited, Osaka (JP)" and insert
-- [73] Assignee: Suntory Flowers Limited, Tokyo (JP). --

Signed and Sealed this

Twenty-seventh Day of January, 2004

JON W. DUDAS
*Acting Director of the United States Patent and Trademark Office*